United States Patent
Proença et al.

(10) Patent No.: US 11,864,874 B2
(45) Date of Patent: Jan. 9, 2024

(54) METHOD, APPARATUS AND COMPUTER PROGRAM FOR DETERMINING A BLOOD PRESSURE VALUE

(71) Applicant: CSEM Centre Suisse d'Electronique et de Microtechnique SA - Recherche et Développement, Neuchâtel (CH)

(72) Inventors: Martin Proença, Marly (CH); Josep Sola i Caros, Corcelles (CH); Mathieu Lemay, St-Sulpice (CH); Christophe Verjus, Neuchâtel (CH)

(73) Assignee: CSEM CENTRE SUISSE D'ELECTRONIQUE ET DE MICROTECHNIQUE SA—RECHERCHE ET DÉVELOPPEMENT, Neuchâtel (CH)

( * ) Notice: Subject to any disclaimer, the term of this patent is extended or adjusted under 35 U.S.C. 154(b) by 564 days.

(21) Appl. No.: 15/543,299

(22) PCT Filed: Jun. 18, 2015

(86) PCT No.: PCT/EP2015/063765
§ 371 (c)(1),
(2) Date: Jul. 13, 2017

(87) PCT Pub. No.: WO2016/138965
PCT Pub. Date: Sep. 9, 2016

(65) Prior Publication Data
US 2017/0360314 A1    Dec. 21, 2017

(51) Int. Cl.
*A61B 5/021* (2006.01)
*A61B 5/00* (2006.01)
(Continued)

(52) U.S. Cl.
CPC ...... *A61B 5/02116* (2013.01); *A61B 5/02125* (2013.01); *A61B 5/02154* (2013.01);
(Continued)

(58) Field of Classification Search
CPC . A61B 5/021; A61B 5/02108; A61B 5/02116; A61B 5/02125; A61B 5/02154;
(Continued)

(56) References Cited

U.S. PATENT DOCUMENTS 4,860,759 A * 8/1989 Kahn ................... G16H 40/63
600/481
5,140,990 A 8/1992 Jones et al.
(Continued)

FOREIGN PATENT DOCUMENTS

CN    104116503 A    10/2014
EP    0956813 A1    11/1999
(Continued)

OTHER PUBLICATIONS

International Search Report for PCT/EP2015/063765 dated Mar. 15, 2016.
Written Opinion for PCT/EP2015/063765 dated Mar. 15, 2016.

*Primary Examiner* — Chao Sheng
(74) *Attorney, Agent, or Firm* — Pearne & Gordon LLP

(57) ABSTRACT

Method for determining a blood pressure value including the steps of: providing a pulsatility signal, determining a time-related feature and a normalized amplitude-related feature on the basis of the pulsatility signal; and calculating a blood
(Continued)

pressure value on the basis of a blood pressure function depending on the time-related feature, the normalized amplitude-related feature and function parameters.

19 Claims, 6 Drawing Sheets

(51) Int. Cl.
    *A61B 5/024*     (2006.01)
    *A61B 5/0215*     (2006.01)
    *A61B 5/0535*     (2021.01)

(52) U.S. Cl.
    CPC ...... *A61B 5/02156* (2013.01); *A61B 5/02416* (2013.01); *A61B 5/7221* (2013.01); *A61B 5/7235* (2013.01); *A61B 5/7278* (2013.01); *A61B 5/02108* (2013.01); *A61B 5/02438* (2013.01); *A61B 5/0535* (2013.01); *A61B 2562/0219* (2013.01)

(58) Field of Classification Search
    CPC ............ A61B 5/02156; A61B 5/02416; A61B 5/02438; A61B 5/7221; A61B 5/7235; A61B 5/7278; A61B 5/0535; A61B 2562/0219

See application file for complete search history.

(56) References Cited

U.S. PATENT DOCUMENTS

| | | | | |
|---|---|---|---|---|
| 5,699,807 | A | * | 12/1997 | Motogi ............... A61B 5/02116 600/490 |
| 6,027,455 | A | * | 2/2000 | Inukai ................ A61B 5/02125 600/485 |
| 7,238,159 | B2 | | 7/2007 | Banet et al. |
| 7,326,180 | B2 | | 2/2008 | Tanabe et al. |
| 8,398,556 | B2 | | 3/2013 | Sethi et al. |
| 2002/0193692 | A1 | * | 12/2002 | Inukai .................... A61B 5/021 600/500 |
| 2005/0228298 | A1 | | 10/2005 | Banet et al. |
| 2008/0039731 | A1 | * | 2/2008 | McCombie ........ A61B 5/02255 600/485 |
| 2009/0326393 | A1 | | 12/2009 | Sethi et al. |
| 2011/0196244 | A1 | | 8/2011 | Ribas Ripoll et al. |
| 2014/0073951 | A1 | | 3/2014 | Engelbrecht et al. |
| 2014/0187884 | A1 | * | 7/2014 | Addison .............. A61B 5/7235 600/324 |
| 2014/0288445 | A1 | * | 9/2014 | Makkonen ......... A61B 5/02108 600/490 |
| 2015/0057554 | A1 | | 2/2015 | Watson et al. |

FOREIGN PATENT DOCUMENTS

| | | |
|---|---|---|
| JP | H10184 A | 1/1998 |
| JP | 2000217796 A | 8/2000 |

\* cited by examiner

METHOD, APPARATUS AND COMPUTER PROGRAM FOR DETERMINING A BLOOD PRESSURE VALUE

FIELD OF THE INVENTION

The present invention concerns a method, apparatus and computer program for determining a blood pressure value.

DESCRIPTION OF RELATED ART

Blood pressure is the pressure exerted by circulating blood upon the walls of blood vessels. A person's blood pressure is usually expressed in terms of the systolic pressure (maximum pressure within an artery during the cardiac cycle), diastolic pressure (minimum pressure within an artery during the cardiac cycle) or pulse pressure (the difference between the systolic and the diastolic pressure values).

Systolic, diastolic and pulse pressure values are used to detect certain health or fitness states of a body and/or to detect diseases.

However, to measure systolic, diastolic or pulse pressure values requires measuring a blood pressure signal via an invasive sensor (sensors placed within an artery).

In the recent time, there were many attempts to provide estimates of blood pressure values on the basis of pulsatility signals, instead of invasive blood pressure signals. Pulsatility signals have the advantage that are easy to be measured non-invasively. These attempts have even increased because of the commercialization of low quality sensors that can be used in wearable devices, e.g. like a photoplethysmogram (PPG) implemented in consumer electronics.

FIG. 1 shows an example of a pulsatility signal 1 for one heart beat. A pulsatility signal 1 is the superposition of the forward pulsatility signal 2 generated by a forward pressure wave propagating within the artery, and the backward pulsatility signal 3 generated by a pressure wave reflecting back within the artery.

Conventionally, blood pressure values are obtained by analyzing the shape and waveforms of such pulsatility signals. Unfortunately, pulsatility signals are signals related to the blood pressure signals, but are not real blood pressure signals. The amplitude and shape distortions of pulsatility signals have been shown to lead to large errors on the estimation of blood pressure values. In particular, the values of DP (diastolic pressure), SP (systolic pressure), P1 (central initial systolic peak) and ESP (pressure at the end of systole) of a pulsatiliy signal do correspond neither in amplitude nor in timing with the DP, SP, P1 and ESP values of the underlying blood pressure signal.

However, because of the major advantage of using pulsatility signals instead of invasive blood pressure signals, several attempts to derive BP values from pulsatility signals are disclosed in the state of the art:

U.S. Pat. No. 5,140,990 discloses a mapping of PPG signal amplitudes into BP values according to a physiological model.

JP2000217796 discloses the mapping of several features extracted from the second derivative of a PPG signal into a BP value.

U.S. Pat. No. 7,238,159 discloses calculating a BP-related value from the parameters of a mathematical model fitted to a PPG waveform.

U.S. Pat. No. 7,326,180 discloses the comparison of a BP value against features calculated from a pulse wave monitor: comparison is done in order to evaluate the cardiovascular status of a patient.

US2011/0196244 discloses an apparatus to measure BP by means of processing a PPG signal. The PPG signal is processed by an ARMA filter and a random forest operator.

U.S. Pat. No. 8,398,556 discloses the calculation of a BP value from a feature based on the area under a portion of a PPG waveform.

CN104116503 discloses a non-invasive continuous blood pressure measuring method comprising the steps of collecting pulse data, extracting characteristic parameters from the pulse data, wherein the characteristic parameters comprise the main wave amplitude, the aorta distention pressuring reducing point, the dicrotic notch amplitude, the dicrotic wave amplitude, the rapid ejection period of the ventriculus sinister, the systole of the ventriculus sinister, the relaxation period of the ventriculus sinister and the pulsation period.

US2005228298 discloses a monitoring device capable of determine a plurality of vital signs of the user when a user's wrist is at rest using a motion sensor disposed within a wrist module that is attached to the user's wrist.

EP0956813 discloses an apparatus for non-invasive estimation of intra-arterial blood pressure.

US2009326393 discloses a method for non-invasive continuous blood pressure determination wherein a PPG signal is received and locations of pulses within the PPG signal are identified.

US2015057554 discloses a method and a device for blood pressure monitoring wherein the device includes a memory storing instructions for receiving one or more signals representative of one or more patient parameters.

US2014073951 discloses a physiological monitoring system may process a physiological signal such a photoplethysmograph signal from a subject.

However, all those features for the blood pressure value are not sufficiently robust against gain changes due to electronic drifts, skin colors, sensor-skin interface and/or do not provide blood pressure measurements sufficiently accurate.

BRIEF SUMMARY OF THE INVENTION

The object is to provide a method, an apparatus and a computer program for determining a blood pressure value which yields a robust and accurate value for the blood pressure from the pulsatility signal.

The object is solved by the independent claims.

The combination of a time-related feature (comprising a time duration within a pulse) and a normalized amplitude-related feature (and not a non-normalized amplitude-related feature), to calculate the blood pressure value gives an accurate and robust estimate for the blood pressure value.

The combination of a time-related feature and an amplitude-related feature in a single blood pressure function has been found to provide highly reliable blood pressure values. Because of the fact that the information contained in both features is independent and complementary, this combination overcomes the performances of known methods for determining blood pressure values using a pulsatility signal. In addition, the use of a normalized amplitude-related feature (instead of an amplitude-related feature) makes the value even more independent from electronic drifts, skin colors and sensor-skin interface, facilitating the implementation of the method of the invention in low-cost consumer electronic devices. Another advantage is that the method disclosed herein can be applied on very simple pulsatility signals such as photoplethysmogram signals.

The dependent claims refer to advantageous embodiments of the invention.

BRIEF DESCRIPTION OF THE DRAWINGS

The invention will be better understood with the aid of the description of an embodiment given by way of example and illustrated by the figures, in which.

DETAILED DESCRIPTION OF POSSIBLE EMBODIMENTS OF THE INVENTION

Figure 2:
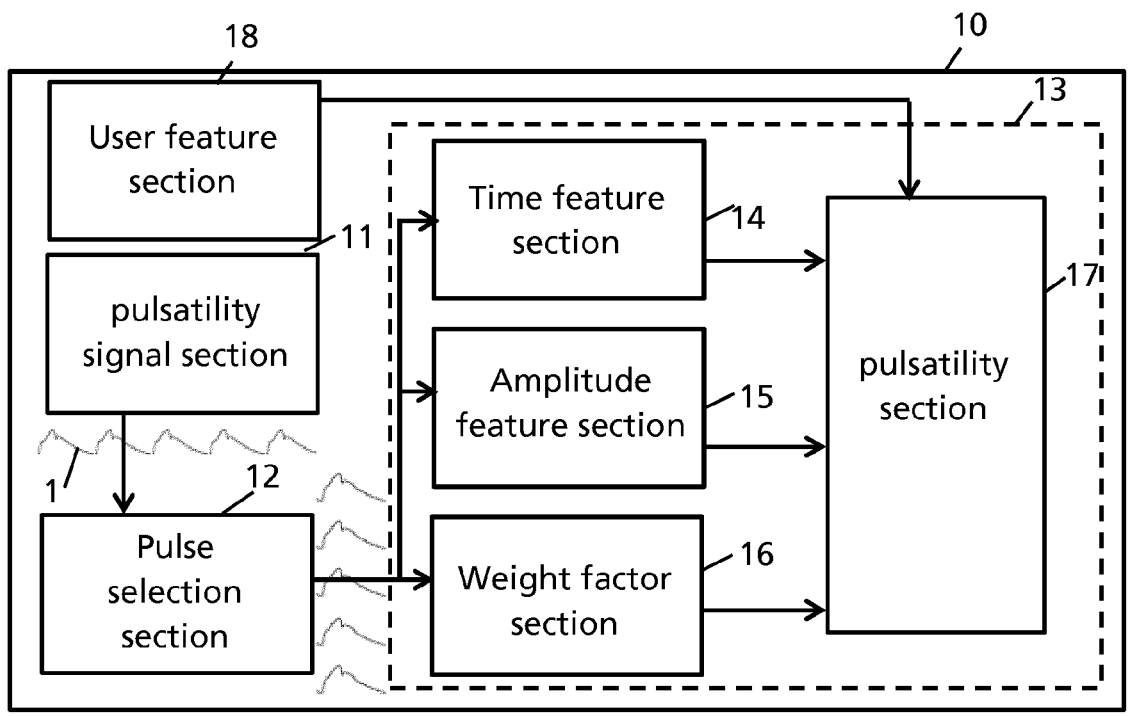
FIG. 2 shows an embodiment of the apparatus for determining a blood pressure value.

FIG. 2 shows an embodiment of the apparatus 10 for determining a blood pressure value. The apparatus 10 comprises a pulsatility signal section 11, a pulse selection section 12, a calculation section 13 and a user feature section 18.

The pulsatility signal section 11 is configured to provide a pulsatility signal. In one embodiment, the pulsatility signal section 11 could be simply an interface configured to receive data representing a pulsatility signal. In another embodiment, the pulsatility signal section 11 could be or comprise a pulsatility sensor for measuring the pulsatility signal of a user. A pulsatility signal can be defined as a signal containing information on the periodic variation of blood flow and arterial diameter of a given segment of the arterial tree. The periodic variations are typically generated by the arrival of a pressure pulse at the given segment of the arterial tree.

Figure 3:
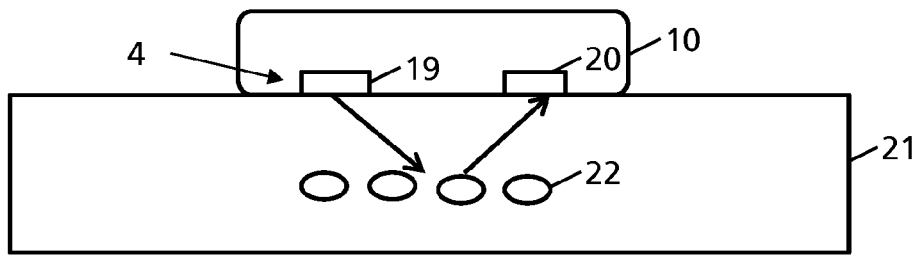
FIG. 3 shows a wrist device with a reflective PPG pulsatility sensor, according to an embodiment.
Figure 4:
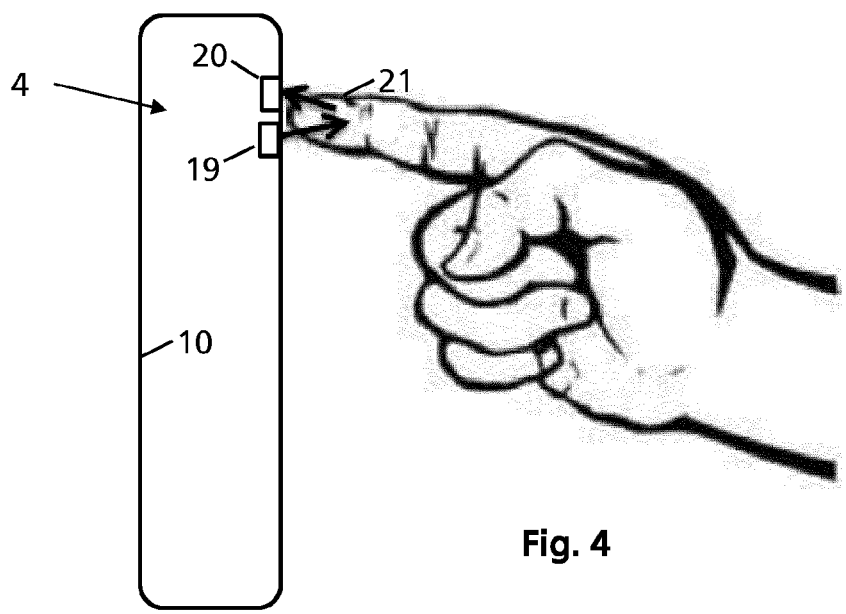
FIG. 4 shows a smartphone with a reflective PPG pulsatility sensor, according to an embodiment.
Figure 5:
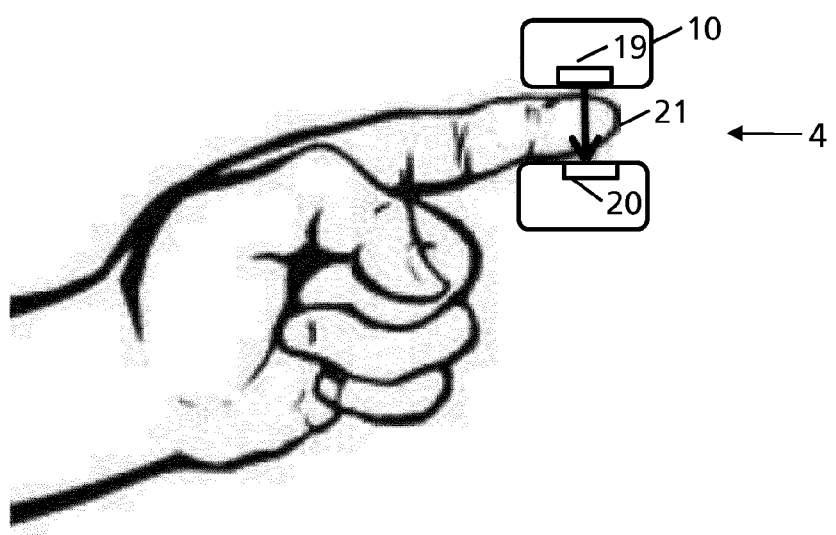
FIG. 5 shows a fingertip device with a transmission PPG pulsatility sensor, according to an embodiment.
Figure 6:
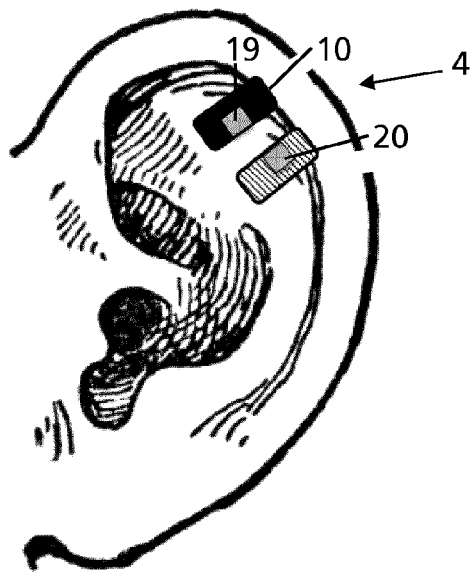
FIG. 6 shows an ear device with a transmission PPG pulsatility sensor, according to an embodiment.

In one embodiment, the pulsatility sensor is a PPG sensor. The PPG sensor can be transmission-based or reflective. FIG. 3 shows an example apparatus 10 with a reflective PPG sensor 4. The apparatus 10 is realized in a wrist device with a light source 19 and a light detector 20 on the side of the wrist device being in contact with the arm skin 21 of a user. Due to the pulsatility of blood flow through the tissue in the subcutaneous vasculature 22, the reflective index of the skin 21 changes. The pulsatility signal of the user can be measured on the basis of the reflective index of the skin 21. The wrist device can comprise also the sections 12 and/or 13 and/or 18 forming the complete apparatus 10. Alternatively, the sections 12 and/or 13 and/or 18 can be arranged in another device of the apparatus 10 connected with the wrist device (e.g. by a cable or a wireless connection). The wrist device 10 can be for example a wrist device like a watch connected to a smart phone. FIG. 4 shows another embodiment of the apparatus 10 realized in a smartphone with the light source 19 and the light detector 20. The light source 19 can for example be realized by a flash of the smart phone 10. The light detector 20 can for example be realized by a camera (e.g. CCD) of the smartphone 10. FIG. 5 shows another embodiment of the apparatus 10 comprising a fingertip device with a transmission PPG sensor 4 with the light source 19 and the light detector 20. The fingertip device can comprise also the sections 12 and/or 13 and/or 18 forming the complete apparatus 10. Alternatively, the sections 12 and/or 13 and/or 18 can be arranged in another device of the apparatus 10 connected with the fingertip device. An alternative transmission PPG sensor 4 can be arranged at the ear. Such a transmission PPG sensor 4 can for example be included in a hearing aid device.

Figures 7, 8:
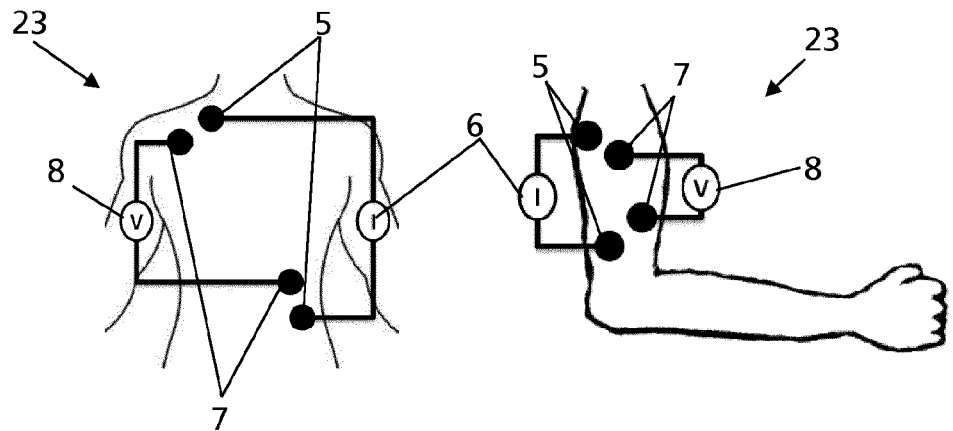
FIG. 7 shows a chest device with an impedance pulsatility sensor, according to an embodiment.
FIG. 8 shows an arm device with an impedance pulsatility sensor, according to an embodiment.
Figure 9:
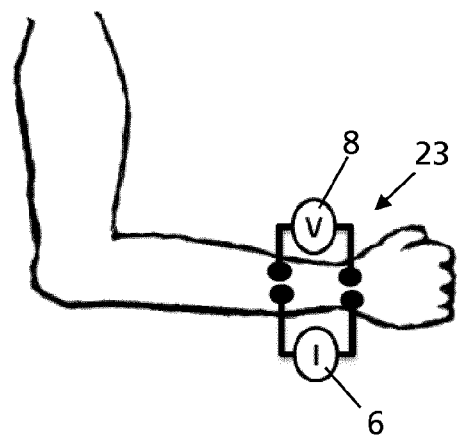
FIG. 9 shows a wrist device with an impedance pulsatility sensor, according to an embodiment.
Figure 10:
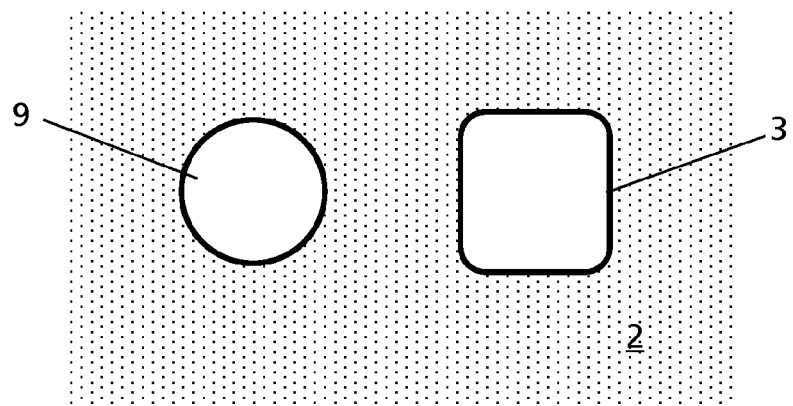
FIG. 10 shows an implanted accelerometer pulsatility sensor, according to an embodiment.
Figure 11:
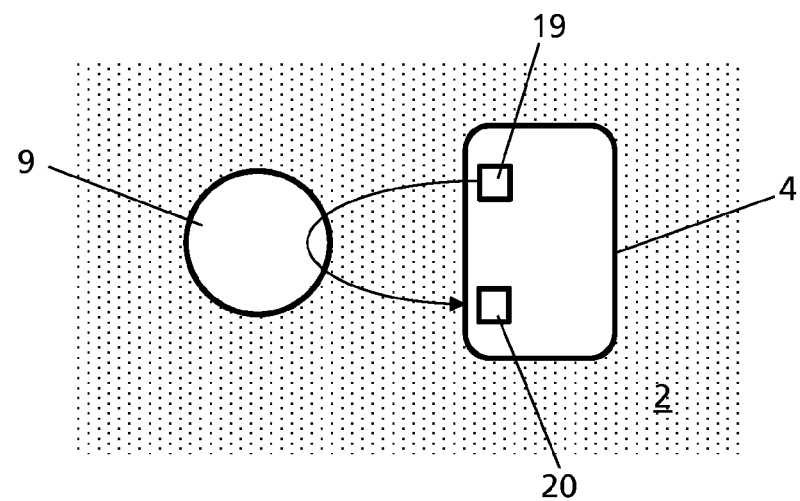
FIG. 11 shows an implanted PPG pulsatility sensor, according to an embodiment.
Figure 12:
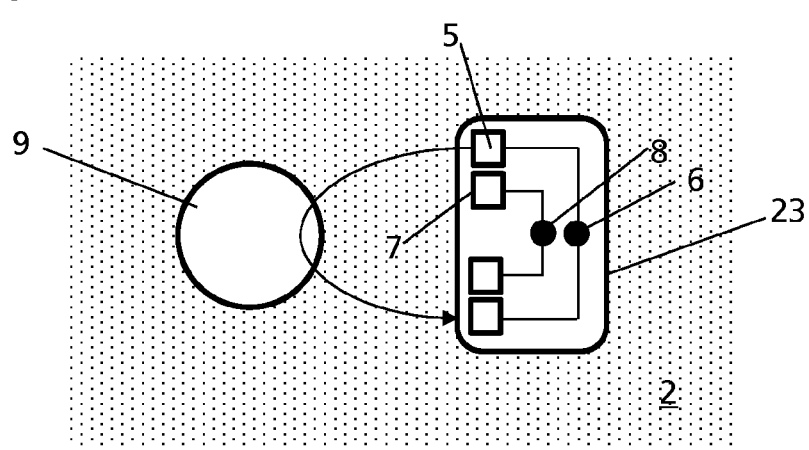
FIG. 12 shows an implanted impedance pulsatility sensor, according to an embodiment.

However, a pulsatility sensor is not restricted to PPG sensors. Also bioimpedance pulsatility sensors are possible as shown in FIGS. 7 to 9. Such a bioimpedance sensor 23 comprises two electrodes 5 for injecting a current 6 and two further electrodes 7 for measuring a voltage 8. This allows also to measure the pulsatility signal. FIG. 7 shows a chest device with an impedance pulsatility sensor. FIG. 8 shows an arm device with an impedance pulsatility sensor 23. FIG. 9 shows a wrist device with an impedance pulsatility sensor 23. The pulsatility sensors where non-invasive sensors. Also implantable pulsatility sensors are possible. The pulsatility signal can for example be measured by an implanted accelerometer sensor 3 implanted in the body tissue 2 in the vicinity of an artery 9 (see FIG. 10). The pulsatility signal can for example be measured by an implanted PPG sensor 4 implanted in vicinity of an artery (see FIG. 11). The pulsatility signal can for example be measured by an implanted impedance sensor 23 implanted in vicinity of an artery 9 (see FIG. 12). The pulsatility signal can for example be measured by an invasive arterial sensor implanted within an artery (not shown).

Figure 1:
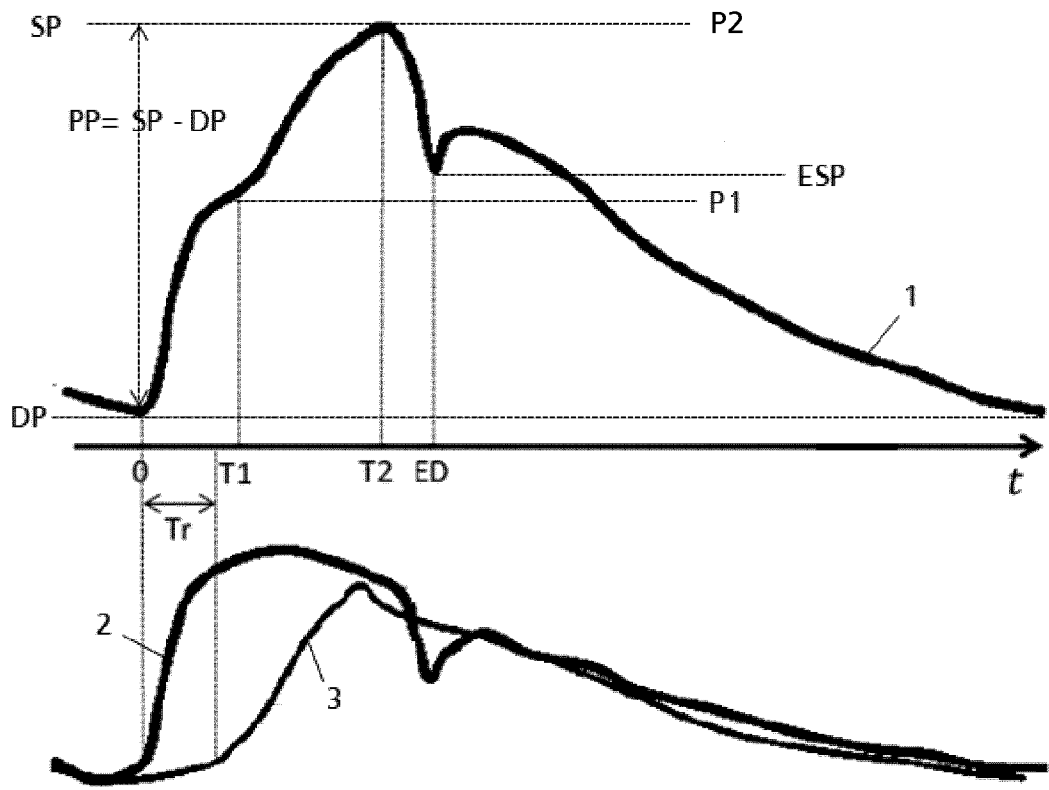
FIG. 1 shows an example of a typical pulsatility signal.

The pulsatility signal 1 of a user is a signal representing the pulsatility amplitude of blood flow through the tissue over the time of the user as shown in FIG. 1. The pulsatility signal is a periodic signal with the period given by the heartbeat of the user. The pulsatility signal consists therefore of a sequence of pulses. FIG. 1 shows one exemplary pulse of the pulsatility signal 1.

The pulse selection section 12 determines at least one pulse in the pulsatility signal 1 of the user. In a preferred embodiment, the pulse selection section 12 selects a plurality of pulses which are given to the calculation section 13. The plurality of pulses can be a fix number of consecutive pulses. Preferably, N consecutive pulses of the pulsatility signal are identified and M<N pulses of the N pulses are selected to be given to the calculation section 13. The M pulses can be selected on the basis of a quality criterion. The quality criterion can be defined to identify the presence of a measurement artifact. For example, because measurement artifacts tend to be associated to very large amplitude signals, the (M-N) pulses with the largest amplitudes (e.g. largest SP or largest total surface under the pulse) can be removed. In another embodiment, only one pulse can be selected and given to the calculation section 13. This is in particular advantageous for high quality pulsatility sensor and/or for high time resolution applications. In one embodiment, the start and end time of each pulse can be detected on the basis of signal analysis. Alternatively, the start and/or end point of each pulse can be detected on the basis of a second measurement. The second measurement should depend also on the heartbeat. This second measurement can be for example an electrocardiogram (ECG) signal from which the start time of each pulse (corresponding to the end time of the previous pulse) can be retrieved. The ECG signal can therefore be used as trigger signal for finding the start of each pulse of the pulsatility signal 1 of the user. The second measurement can for example also be a PPG signal, a bioimpedance signal or any suitable pulsatility signal.

The user feature section 18 is configured to provide user feature UF about the user related to the pulsatility signal 1. The user feature UF can be used in the calculation section 13. The user feature section 18 can comprise a storage section for storing the user feature(s). The user feature section 18 can alternatively or additionally comprise a user interface for entering the user feature(s). Examples for user features UF are one or any combination of gender, age, height, body mass index, . . . . Gender can be mathematically expressed by a binary value, e.g. by 1 for female and 0 for male or vice versa. However, the user feature section 18 is optional and is not necessary, if the blood pressure value calculated in the calculation section 13 is independent of a user feature.

The calculation section 13 comprises a time feature section 14, an amplitude feature section 15, a weight factor section 16 and a blood pressure section 17. The calculation section 13 is configured to calculate a blood pressure value on the basis of the pulse(s) received from the pulse selection section 12. In one embodiment, the calculation section 13 calculates one blood pressure value on request. In another embodiment, the calculation section 13 calculates continuously new blood pressure values, wherein for each calculation period one blood pressure value is calculated. In the latter case, the pulse selection section 12 gives within each calculation period one pulse or M pulses of the pulsatility signal 1 used for the calculation of a blood pressure value for this calculation period. In the following, the functioning of the calculation section 13 and its components is described for the calculation of one blood pressure value. For the calculation of a plurality of blood pressure values, this functioning is simply repeated.

The time feature section 14 is configured to determine at least one time-related feature TRF on the basis of the pulse(s) received from the pulse selection section 12. Preferably, the at least one time-related feature $TRF_i$ feature is computed from each pulse i of the M pulses of the pulsatility signal 1 received from the pulse selection section 12 so that for each time-related feature M values will be calculated. However, it is also possible to compute a time related feature TRF on the basis of M pulses, e.g. the heart rate. If only one pulse is received from the pulse selection section 12 for one blood pressure calculation period, the at least one time related feature TRF is computed only for this pulse. A time-related feature is preferably any time duration within a pulse, the inverse of such a time duration, or any other value computed from such a time duration, e.g. the average of a time duration or its inverse of a plurality of peaks. Examples for such a time-related feature are the time to first peak T1 (duration between the start time of the pulse and its first peak or shoulder of pulse), time to second peak T2 (duration between start time of pulse and second peak or shoulder of pulse), inverse time to first peak 1/T1, inverse of time to second peak 1/T2, time between first and second peak T2−T1, time to reflection Tr (duration between start time of pulse and arrival time of the reflected (backward) wave), ejection duration ED (duration between start time of pulse and time of closure of the aortic valve), heart rate. The detection and/or calculation of these time-related features TRF is well-known in the state of the art and is not described here in more detail. The at least one time-related feature TRF comprises L equal one, two, or more distinct time-related features $TRF_j$. In the case that for each pulse i of the M pulses, L distinct time-related features $TRF_{i,j}$ are calculated, for each calculation period, M*L time-related features $TRF_{i,j}$ are calculated.

Figure 13:
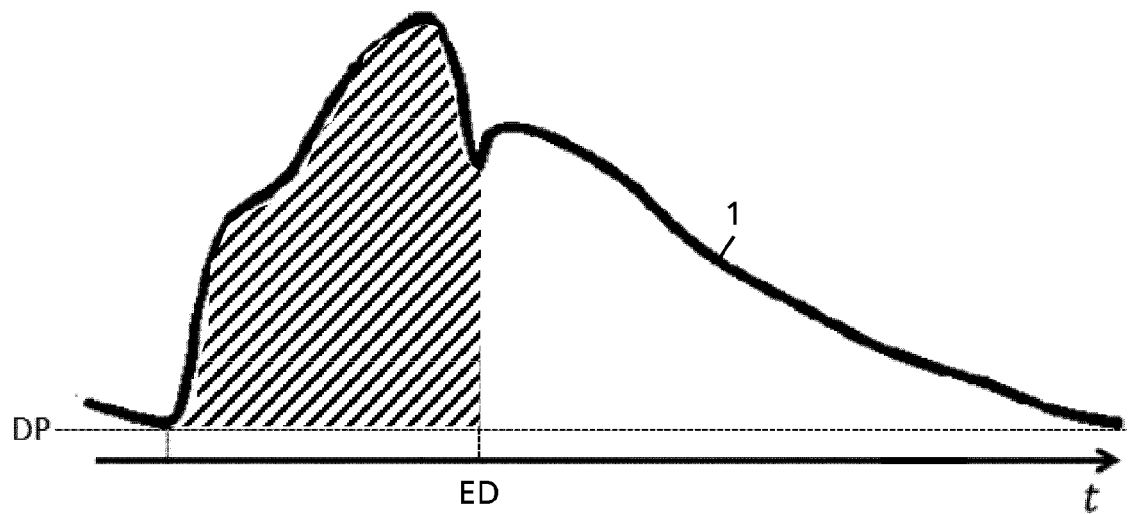
FIG. 13 shows the ejection area under the pulsatility signal.
Figure 14:
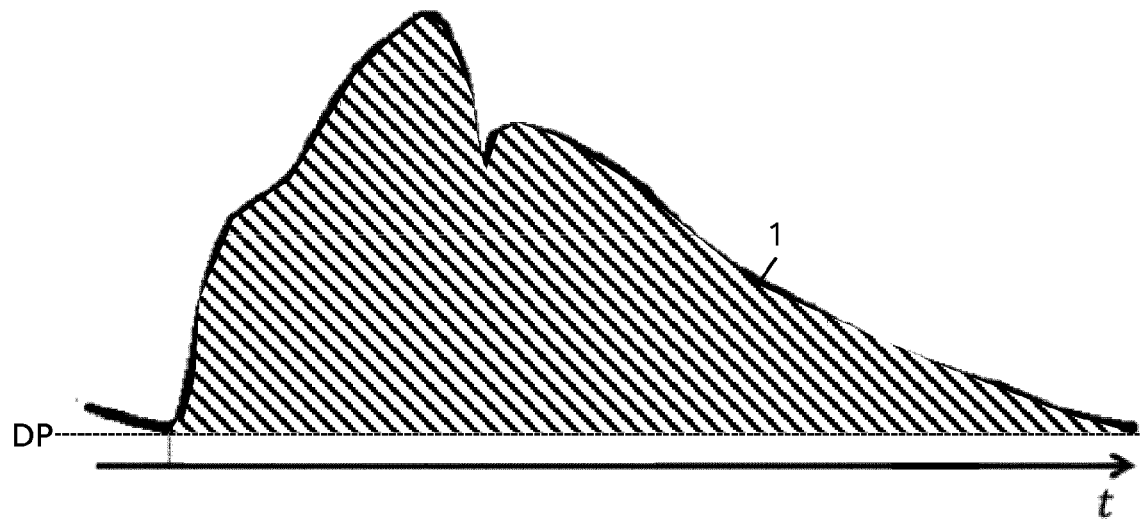
FIG. 14 shows the total area under the pulsatility signal.

The amplitude feature section 15 is configured to determine at least one normalized amplitude-related feature NAF on the basis of the pulse(s) received from the pulse selection section 12. Preferably, at least one normalized amplitude-related $NAF_i$ feature is computed from each pulse i of the M pulses of the pulse pressure signal 1 received from the pulse selection section 12. However, it is also possible to compute a normalized amplitude-related feature NAF on the basis of the average of the M pulses. If only one pulse is received from the pulse selection section 12 (e.g. for one/each calculation period), the at least one normalized amplitude-related feature NAF is computed only for this pulse. An amplitude-related feature AF is preferably any value based on an amplitude value of the pulsatility signal 1. A normalized amplitude-related feature NAF is an amplitude-related feature normalized by another amplitude-related feature. Normalization is preferably performed by a ratio of two amplitude-related features NAF=AF1/AF2. In one embodiment, such a normalized amplitude-related feature NAF is a normalized end-systolic pressure nESP=(ESP−DP)/PP calculated by the difference of the absolute end-systolic pressure ESP and the diastolic pressure DP divided or normalized by the pulse pressure PP. In one embodiment, such a normalized amplitude-related feature NAF is a first augmentation index AIx=(P2−P1)/PP calculated by the difference of the pressure amplitude of the second peak P2 and the pressure amplitude of the first peak P1 divided or normalized by the pulse pressure PP. In one embodiment, such a normalized amplitude-related feature NAF is a second augmentation index AIp=(P2−DP)/(P1−DP) calculated by the difference of the pressure amplitude of the second peak P2 and the diastolic pressure amplitude DP divided or normalized by the difference of the pressure amplitude of the first peak P1 and the diastolic pressure amplitude DP. In one embodiment, such a normalized amplitude-related feature NAF is a normalized ejection area nEjecA (see FIG. 13). The normalized ejection area is calculated as the surface under the pulsatility signal 1 for the ejection duration ED divided or normalized by the area under the pulsatility signal 1 for the duration of this pulse (see FIG. 14). The surface under the pulsatility signal 1 for the ejection duration ED does preferably not include the surface DP*ED below the diastolic pressure DP as shown in FIG. 13, but it is also possible to use the surface under the pulsatility signal 1 for the ejection duration ED with the surface DP*ED below the diastolic pressure DP. The surface under the pulsatility signal 1 for the duration T of the pulse does preferably not include the surface DP*T below the diastolic pressure DP as shown in FIG. 14, but it is also possible to use the surface under the pulsatility signal 1 for the pulse duration T with the surface DP*T below the diastolic pressure DP, if the surface DP*ED below the diastolic pressure is also considered for the ejection duration. The detection and/or calculation of the mentioned normalized amplitude-related features NAF are well-known and are therefore not described in more detail here. The at least one normalized amplitude-related features NAF comprises K equal one, two, or more distinct normalized amplitude-related features $NAF_j$. In the case that for each pulse i of the M pulses, K distinct normalized amplitude-related features $NAF_{i,j}$ are calculated so that, for each calculation period, M*K normalized amplitude-related features $NAF_{i,j}$ are calculated.

The weight factor section 16 is optional and only necessary, if the calculation section 13 calculates a weighted average of the time-related feature(s) TRF and/or the normalized amplitude-related feature(s) NAF over a plurality of pulses with weights depending on the plurality of pulses. The weight factor section 16 is configured to calculate a weighting factor $WF_i$ for each pulse i of the plurality M of pulses received from the pulse selection section. The weighting factor $WF_i$ is preferably calculated on the basis of a quality criterion of the pulse. This could be for example the error of the pulse i relative to the average of the M pulses. Such an error can be calculated by a normalized accumulation of the errors between the points of the average pulse and the corresponding points of the respective pulse i. The errors can be the absolute errors, the quadratic errors, or any other measure for the error.

In one embodiment, the weighting factor $WF_i$ is based on a morphological error. A morphological error can be defined as a value describing the morphology of a particular pulse. Typical morphologies have been defined in the literature (Nichols et al, "McDonald's blood flow in arteries", Oxford University Press 2005, ISBN 0 340 80941 8) and describe the timing and amplitude relationships between P1, P2, T1 and T2 (see FIG. 1). These morphologies may change among subjects depending on their age and cardiovascular status. Typical morphologies are Type C (associated to young subjects), Type B (associated to mid-age subjects), and Type A and D (associated to elderly and ill subjects). Other sub-morphologies can be defined as well. In a preferred embodiment, the weighting factor $WF_i$ of the pulse i depends on how much the pulsatility signal i matches to a typical morphology. This could be for example the error of the pulse i relative to the most likely subject pulse morphology according to his age and health status.

In a yet preferred embodiment, the weighting factor $WF_i$ of the pulse i depends on the morphological error of the pulse i and the error of the pulse i relative to the average of the M pulses. In one embodiment, the calculated quality criterion of each pulse i, e.g. the mentioned error and/or the morphological error, is compared to a quality threshold. Based on the comparison (above or below) the weight factor $WF_i$ is set to zero (0) for bad quality and one (1) for a good quality. According to this binary weighting procedure only the pulses with a certain quality are used.

The pulsatility signal (1) can comprise a further plurality of pulses being larger than the plurality of pulses, wherein the plurality of pulses is selected among the further plurality of pulses by removing the pulses with the largest amplitude.

The blood pressure section 17 is configured to calculate a blood pressure value on the basis of the at least one time-related feature TRF and the at least one amplitude-related feature NAF. In one (optional) embodiment, a blood pressure function for calculating the blood pressure value depends additionally on the at least one user feature. In one embodiment, a blood pressure function for calculating the blood pressure value depends linearly on the at least one time-related feature TRF and the at least one normalized amplitude-related feature NAF. In one embodiment, a blood pressure function for calculating the blood pressure value depends linearly on the used feature(s) (TRF, NAF and/or UF). Preferably, each feature is weighted relative to the other features by linear feature coefficients, like the linear time coefficient(s) kt, the linear amplitude coefficient(s) ka and the linear user coefficient ku. The linear time coefficient(s) kt and the linear amplitude coefficient(s) ka and, if user feature(s) UF is/are considered, a linear user coefficient ku fix the relative influence of the time-related feature(s) TRF and the normalized amplitude-related feature(s) and, if user features UF are considered, the user feature UF on the blood pressure value. If one or more of the features are calculated for a plurality of pulses, the feature coefficient k remains the same for the same feature for all pulses. In one embodiment, the blood pressure function depends on the at least one time-related feature $TRF_i$ and the at least one amplitude-related feature $NAF_i$ of a plurality of pulses i. In this case, the function for the blood pressure value BP is direct proportional to $$\sum_{i=1}^{M} WF_i \cdot \left[ \left( \sum_{j=1}^{L} kt_j \cdot TRF_{i,j} \right) + \left( \sum_{j=1}^{K} ka_j \cdot NAF_{i,j} \right) \right].$$

with M pulses, L time-related features TRF and K normalized amplitude-related features NAF with L being one, two or more and with K being one, two or more. If M=1 only one pulse is considered. If L=1, only one time-related feature TRF is considered. If K=1, only one normalized amplitude-related feature is considered. Therefore, the linear feature coefficient might be different for each feature, but is the same for the same feature of different pulses. Considering also user features UF, the function for the blood pressure value BP is direct proportional to $$\sum_{i=1}^{M} WF_i \cdot \left[ \left( \sum_{j=1}^{L} kt_j \cdot TRF_{i,j} \right) + \left( \sum_{j=1}^{K} ka_j \cdot NAF_{i,j} \right) + \left( \sum_{j=1}^{U} ku_j \cdot UF_j \right) \right].$$

with M pulses, L time-related features TRF, K normalized amplitude-related features NAF and U user features with L being one, two or more, with K being one, two or more and U being one, two or more. If U=1, only one user feature is considered. Obviously, the term of the user features could be taken out of the sum over the pulses, if the weight factors WF sum up to one or if the user coefficients are adapted accordingly.

In one embodiment, the feature coefficients kt, ka, ku are predetermined and stored in a storage section of the blood pressure section 17. In one embodiment, the feature coefficients kt, ka, ku are configurable. The feature coefficients kt, ka, ku can be set by a user or an administrator. The features coefficients kt, ka, ku can also be determined by an automatic process, e.g. a calibration process. The calibration process comprises the step of measuring the blood pressure of the user with an independent sensor and minimizing the error of the blood pressure value calculated by the blood pressure section on the basis of the feature coefficients kt, ka, ku. In medical applications, the apparatus can include a user interface for entering once or periodically blood pressure values measured independently. This allows an online monitoring of the blood pressure of the user which reaches almost the preciseness of traditional cuff measurements, if the independent measurements are measured by cuff measurements of the blood pressure.

The calibration process can further include also the selection of the best time-related features and/or normalized amplitude-related features and/or user-related features among O potential features. This can be performed by performing the above described calibration process for all O! (factorical of O) potential combination of features and select the best combination of feature including at least one time-related feature and at least one normalized amplitude-related feature.

Even if the blood pressure value is calculated without having any absolute pressure amplitude value, the inventive method yields a robust blood pressure value. If the method is used without a calibration on the particular user, the results are still good enough to robustly detect hypotension (low blood pressure), normal blood pressure and hypertension (high blood pressure). If the method is used with a calibration on the particular user, the results yield a good estimate of the blood pressure value which is even good enough for medical applications. Such an algorithm could be used with pulse oximetry fingertip sensors including a PPG transmission sensor as shown in FIG. 5 or for other medical sensors shown for example in FIGS. 6 to 9 and described above. This would allow an online monitoring of the blood pressure with high preciseness instead of the state of the art cuff measurements which can only be repeated in fixed time intervals.

Figure 15:
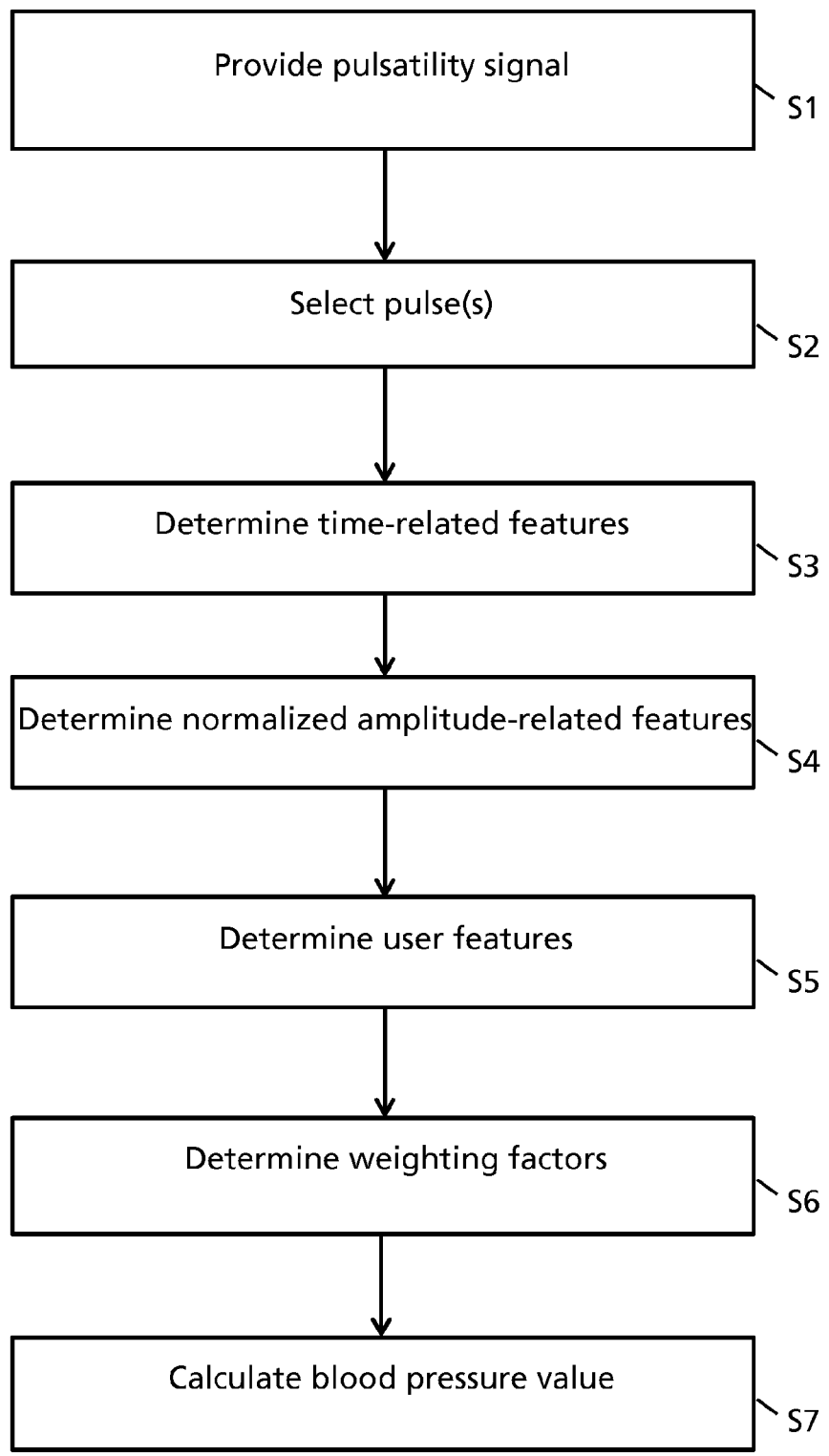
FIG. 15 shows an embodiment of the method for determining a blood pressure value.

FIG. 15 shows an embodiment of the method for determining a blood pressure value.

In step S1, a pulsatility signal of the user is provided as described in more detail with respect to the pulsatility signal section 11. In step S2, a pulse or a number of pulses are selected from the provided blood pressure signal of S1. In step S3, at least one time-related feature is determined for the one pulse or for each of the number of pulses as described in more detail with respect to the time feature section 14. In step S4, at least one normalized amplitude-related feature is determined for the one pulse or for each of the number of pulses as described in more detail with respect to the amplitude feature section 15. In optional step S5, at least one user feature is determined as described in more detail with respect to the user feature section 18. In optional step S6, a weighting factor $WF_i$ is determined for each of the number of pulses as described in more detail with respect to the weight factor section 16. In step S7, the blood pressure value is calculated on the basis of the at least one time-related feature TRF and the at least one normalized amplitude-related feature NAF and optionally on the weighting factors WF and the at least one user feature(s) as described in more detail with respect to the blood pressure section 17.

What is claimed is:

1. Method for determining a blood pressure value comprising the steps of:
    providing a pulsatility signal of a user, the pulsatility signal comprising a plurality of pulses;
    selecting only one pulse of the plurality of pulses of the pulsatility signal;
    for the selected only one pulse, determining a first feature and a second feature on the basis of the pulsatility signal; and
    calculating a blood pressure value on the basis of a blood pressure function depending on the first feature, the second feature, and function parameters, the first feature being a time-related feature comprising a time duration within the selected only one pulse, and the second feature being a normalized amplitude-related feature,
    wherein the calculating does not use a non-normalized amplitude-related feature,
    wherein the normalized amplitude-related feature is an amplitude-related feature normalized by another amplitude-related feature,
    wherein the blood pressure function further linearly depends on a user feature,
    wherein the function parameters comprise a time-related coefficient, an amplitude-related coefficient, and a user coefficient,
    wherein the time-related feature is multiplied with the time-related coefficient, the normalized amplitude-related feature is multiplied with the amplitude-related coefficient before summing the time-related feature with the normalized amplitude-related feature,
    wherein the user feature is multiplied with the user coefficient before adding the user feature to the time-related feature and the normalized amplitude-related feature, and
    wherein the time-related coefficient, the amplitude-related coefficient, and the user coefficient are determined by a calibration process comprising measuring the blood pressure of the user with an independent sensor.

2. Method according to claim 1, wherein the blood pressure function is linear with respect to the time-related feature and the normalized amplitude-related feature.

3. Method according to claim 1, wherein the user feature comprises one or a combination of:
    gender;
    age;
    body mass index; or
    height.

4. Method according to claim 1, wherein the first and second features used for calculating the blood pressure value are automatically determined from a plurality of features.

5. Method according to claim 1, wherein the time related feature is based on one or a combination of:
    time to first peak;
    time to second peak;
    inverse time to first peak;
    inverse of time to second peak,
    time between first and second peak,
    time to reflection,
    ejection duration, or
    heart rate.

6. Method according to claim 1, wherein the normalized amplitude-related feature is based on one or a combination of:
    a normalized end-systolic pressure;
    an augmentation index; or
    a normalized ejection area.

7. Method according to claim 1,
    wherein said time-related feature and said normalized amplitude-related feature are calculated from the selected only one pulse,
    wherein a weighting factor is calculated for the selected only one pulse on the basis of an error of the selected only one pulse relative to an average of the plurality of pulses, and
    wherein the blood pressure function calculates the blood pressure value on the basis of a weighted combination, wherein the time-related feature and the normalized amplitude-related feature of each pulse is weighted with the weighting factor.

8. Method according to claim 7, wherein the weighting factor of the selected only one pulse is calculated on the basis of a match between a morphology of the selected only one pulse and a typical morphology.

9. Method according to claim 1, wherein the step of providing the pulsatility signal comprises the step of measuring the pulsatility signal.

10. Method according to claim 9, wherein the pulsatility signal is measured on the basis of one of a photoplethysmogram, an impedance sensor, an implantable accelerometer sensor, an implantable optical sensor, an implantable impedance sensor or an invasive arterial sensor.

11. A non-transitory computer-readable medium having instructions thereon that when implemented by a processor cause the processor to perform a method comprising:
provide a pulsatility signal of a user, the pulsatility signal comprising a plurality of pulses;
selecting only one pulse of the plurality of pulses of the pulsatility signal;
for the selected only one pulse, determining a time-related feature comprising a time duration within the selected only one pulse and a normalized amplitude-related feature, on the basis of the pulsatility signal; and
calculating a blood pressure value on the basis of a blood pressure function depending on the time-related feature, the normalized amplitude-related feature, and function parameters,
wherein the calculating does not use a non-normalized amplitude-related feature,
wherein the normalized amplitude-related feature is an amplitude-related feature normalized by another amplitude-related feature,
wherein the blood pressure function further linearly depends on a user feature,
wherein the function parameters comprise a time-related coefficient, an amplitude-related coefficient, and a user coefficient,
wherein the time-related feature is multiplied with the time-related coefficient, the normalized amplitude-related feature is multiplied with the amplitude-related coefficient before summing the time-related feature with the normalized amplitude-related feature,
wherein the user feature is multiplied with the user coefficient before adding the user feature to the time-related feature and the normalized amplitude-related feature, and
wherein the time-related coefficient, the amplitude-related coefficient, and the user coefficient are determined by a calibration process comprising measuring the blood pressure of the user with an independent sensor.

12. Apparatus for determining a blood pressure value comprising:
at least one processor configured to:
receive data representing a pulsatility signal of a user, the pulsatility signal comprising a plurality of pulses;
select only one pulse of the plurality of pulses of the pulsatility signal;
calculate a first feature for the selected only one pulse;
calculate a second feature for the selected only one pulse; and
calculate a blood pressure value on the basis of a function depending on the first feature, the second feature, and function parameters, the first feature being a time-related feature comprising a time duration within the selected only one pulse, and the second feature being a normalized amplitude-related feature,
wherein the blood pressure value is not calculated based on a non-normalized amplitude-related feature,
wherein the normalized amplitude-related feature is an amplitude-related feature normalized by another amplitude-related feature,
wherein the blood pressure function further linearly depends on a user feature,
wherein the function parameters comprise a time-related coefficient, an amplitude-related coefficient, and a user coefficient,
wherein the time-related feature is multiplied with the time-related coefficient, the normalized amplitude-related feature is multiplied with the amplitude-related coefficient before summing the time-related feature with the normalized amplitude-related feature,
wherein the user feature is multiplied with the user coefficient before adding the user feature to the time-related feature and the normalized amplitude-related feature, and
wherein the time-related coefficient, the amplitude-related coefficient, and the user coefficient are determined by a calibration process comprising measuring the blood pressure of the user with an independent sensor.

13. Apparatus according to claim 12, wherein said at least one processor is further configured to:
calculate the time-related feature for the selected only one pulse,
calculate the normalized amplitude-related feature for the selected only one pulse, and
calculate the blood pressure value on the basis of a combination of the time-related features and the normalized amplitude-related features of the selected only one pulse.

14. Apparatus according to claim 13, wherein said at least one processor is further configured to:
calculate for the selected only one pulse a weighting factor, and
calculate the blood pressure value on the basis of the weighting factor,
wherein the time-related feature and the normalized amplitude-related feature of the selected only one pulse is weighted with the weighting factor.

15. Apparatus according to claim 13, further comprising a sensor for measuring the pulsatility signal.

16. Apparatus according to claim 15, wherein the sensor is:
a PPG sensor;
an impedance sensor;
an implantable accelerometer sensor;
an implantable optical sensor;
an implantable impedance sensor; or
an invasive arterial sensor.

17. Method for determining a blood pressure value comprising the steps of:
providing a pulsatility signal section comprising a PPG sensor and supplying a single pulsatility signal of a user, said single pulsatility signal comprising a plurality of pulses;
identifying a plurality of consecutive pulses of said single pulsatility signal and selecting only one pulse of the identified plurality of pulses;
for the selected only one pulse, calculating a time-related feature comprising a time duration within the selected only one pulse and a normalized amplitude-related feature;
calculating a blood pressure value on the basis of a blood pressure function depending on the time-related feature, the normalized amplitude-related feature, and function parameters, wherein the calculating does not use a non-normalized amplitude related feature, wherein the normalized amplitude-related feature is an amplitude related feature normalized by another amplitude-related feature, wherein the blood pressure function further linearly depends on a user feature, wherein the function parameters comprise a time-related coefficient, an amplitude-related coefficient, and a user coefficient, wherein the time-related feature is multiplied with the time-related coefficient, the normalized amplitude-related feature is multiplied with the amplitude-related coefficient before summing the time-related feature with the normalized amplitude-related feature, wherein the user feature is multiplied with the user coefficient before adding the user feature to the time-related feature and the normalized amplitude-related feature, and wherein the time-related coefficient, the amplitude-related coefficient, and the user coefficient are determined by a calibration process comprising measuring the blood pressure of the user with an independent sensor.

18. Method according to claim 17, further comprising:

for the selected only one pulse, calculating a weighting factor on the basis of the selected only one pulse relative to the average of the identified plurality of pulses;

weighting the time-related feature and the normalized amplitude related feature of each of the identified plurality of pulses with the weighting factor; and calculating the blood pressure value by using the combination of the weighted time-related and the weighted normalized amplitude-related feature, wherein said time-related feature and said normalized amplitude related feature are calculated from the identified plurality of pulses of the single pulsatility signal.

19. Method for determining a blood pressure value comprising the steps of:

providing a single pulsatility signal section comprising a PPG sensor and supplying a pulsatility signal of a user, said single pulsatility signal comprising a plurality of pulses;

identifying a plurality of consecutive pulses within said single pulsatility signal and selecting only one pulse of the identified plurality of pulses;

for the selected only one pulse, calculating a plurality of time-related features, each time-related feature comprising a time duration within the selected only one pulse, and calculating a plurality of normalized amplitude-related features; and calculating a blood pressure value on the basis of a blood pressure function depending on the plurality of time-related features, the plurality of normalized amplitude-related features, and function parameters, wherein the calculating does not use a non-normalized amplitude related feature, and wherein each normalized amplitude-related feature is an amplitude related feature normalized by another amplitude-related feature, wherein the blood pressure function further linearly depends on a user feature, wherein the function parameters comprise a time-related coefficient, an amplitude-related coefficient, and a user coefficient, wherein each time-related feature of said plurality of time-related features is multiplied with the time-related coefficient, each normalized amplitude-related feature of said plurality of normalized amplitude-related features is multiplied with the amplitude-related coefficient before summing said each time-related feature with said each normalized amplitude-related feature, wherein the user feature is multiplied with the user coefficient before adding the user feature to said each time-related feature and said each normalized amplitude-related feature, and wherein said each time-related coefficient, said each amplitude-related coefficient, and the user coefficient are determined by a calibration process comprising measuring the blood pressure of the user with an independent sensor.

\* \* \* \* \*